(12) United States Patent
Kopas et al.

(10) Patent No.: US 8,524,292 B2
(45) Date of Patent: Sep. 3, 2013

(54) COSMECEUTICAL FORMULATION CONTAINING PALM OILS

(75) Inventors: Patricia McKane Kopas, Atherton, CA (US); George Kopas, Atherton, CA (US)

(73) Assignee: Pacific Specialty Oils, Inc., San Francisco, CA (US)

( * ) Notice: Subject to any disclaimer, the term of this patent is extended or adjusted under 35 U.S.C. 154(b) by 636 days.

(21) Appl. No.: 12/402,330

(22) Filed: Mar. 11, 2009

(65) Prior Publication Data

US 2009/0182051 A1 Jul. 16, 2009

Related U.S. Application Data

(63) Continuation of application No. 10/855,681, filed on May 26, 2004, now Pat. No. 7,531,196.

(60) Provisional application No. 60/475,217, filed on May 30, 2003.

(51) Int. Cl.
*A61K 36/889* (2006.01)
*A61K 8/02* (2006.01)

(52) U.S. Cl.
USPC .......................... 424/727; 424/401; 426/615

(58) Field of Classification Search
USPC ..................................... 424/727; 426/2, 417
See application file for complete search history.

(56) References Cited

U.S. PATENT DOCUMENTS

| | | | |
|---|---|---|---|
| 1,398,947 A | 9/1921 | Hechler |
| 3,615,558 A | 10/1971 | Carlile et al. |
| 3,617,308 A | 11/1971 | Graffelman |
| 3,634,100 A | 1/1972 | Merksem |
| 3,686,240 A | 8/1972 | Kawada et al. |
| RE30,086 E | 8/1979 | Carlile et al. |
| 4,386,111 A | 5/1983 | Van Heteren et al. |
| 4,388,339 A | 6/1983 | Lomneth et al. |
| 4,454,159 A | 6/1984 | Musher |
| 4,842,648 A | 6/1989 | Phadoemchit et al. |
| 4,902,527 A | 2/1990 | Galenkamp et al. |
| 4,960,544 A | 10/1990 | Van Putte et al. |
| 5,000,975 A | 3/1991 | Tomarelli |
| 5,019,668 A | 5/1991 | Keat et al. |
| 5,160,738 A | 11/1992 | Macaulay et al. |
| 5,237,080 A | 8/1993 | Daute et al. |
| 5,431,948 A | 7/1995 | Cain et al. |
| 5,442,082 A | 8/1995 | Uphues et al. |
| 5,545,398 A | 8/1996 | Perricone |
| 5,674,504 A | 10/1997 | Kauffmann |
| 5,786,019 A | 7/1998 | Cain et al. |
| 5,874,117 A | 2/1999 | Sundram et al. |
| 5,882,657 A | 3/1999 | Miguel-Colombel et al. |
| 5,932,261 A | 8/1999 | Unnithan |
| 5,932,275 A | 8/1999 | Nalur |
| 5,945,095 A | 8/1999 | Mougin et al. |
| 6,132,742 A | 10/2000 | Le Bras et al. |
| 6,183,762 B1 | 2/2001 | Deckers et al. |
| 6,238,926 B1 | 5/2001 | Liu et al. |
| 6,277,430 B1 | 8/2001 | Cain et al. |
| 6,319,508 B1 | 11/2001 | Ribier et al. |
| 6,346,236 B1 | 2/2002 | Compton et al. |
| 6,500,479 B2 | 12/2002 | Bhaggan et al. |
| 6,518,226 B2 | 2/2003 | Volker et al. |
| 6,544,938 B1 | 4/2003 | Yarovoy et al. |
| 7,105,195 B2 | 9/2006 | Plank et al. |
| 2002/0025333 A1 | 2/2002 | Agostini et al. |
| 2002/0034577 A1 | 3/2002 | Vogensen et al. |
| 2002/0037882 A1 | 3/2002 | Beindorff et al. |
| 2002/0068076 A1 | 6/2002 | Bras-Roulier et al. |
| 2002/0081366 A1 | 6/2002 | Cain et al. |
| 2003/0026856 A1 | 2/2003 | Aust et al. |
| 2003/0044506 A1 | 3/2003 | Sakai et al. |

FOREIGN PATENT DOCUMENTS

EP 0 081 881 6/1983

OTHER PUBLICATIONS

"Natural Oils and Fats for Cosmetics," Oils Fats Intl. Jan 2003, pp. 18-19.
Ping and May, "Valuable phytonutrients in commercial red palm olein," Palm Oil Developments, 32:20-25, 2000.
Horrobin, "Evening primrose oil—miracle worker of the eighties," Health Quarterly (1981).
"Tocomin and Tocomax," Neurosci. Lett. (1995) 195:179-182.
Osborn and Akoh, "Structured lipids—novel fats with medical, nutraceutical, and food applications," Comp. Rev. Food Sci. Food Safety (2002) 1:93-103.
Serbinova and Packer, "Antioxidant and biological activities of palm oil vitamin E," Food Nutrition Bull. (1994) 15:1-7. Rukmini, "Red palm oil to combat vitamin a deficiency in developing countries," Food Nutrition Bull. (1994) 15:1-5.
May, "Palm oil carotenoids," Food Nutrition Bull. (1994) 15:1-14.
Sambanthamurthi, et al., "Chemistry and biochemistry of palm oil," Prog. Lipid Res. (2000) 39:507-558.
Campbell, et al., "Food fats and oils," (1999) Institute of Edible Oils, Washington, DC., pp. 1-41.
Oliveira, et al., "A hybrid neural network model applied to the biomodification of palm kernel oil in SCCO2," 4th Intl. Symposium on High Pressure Process Technol. and Chem Eng., Sep. 22-25, 2000, Venice, Italy.
Oliveira and Alves, "Enzymatic alcoholysis of palm and palm kernel oils: optimization by statistical analysis," 4th Intl. Symposium on High Pressure Process Technol. and Chem Eng., Sep. 22-25, 2000, Venice, Italy.
Sharma, et al., "Production, purification, characterization, and applications of lipases," Biotechnol. A dv. (2001) 19:627-662.
Partially Hydrogentated Oils, www.tirtiaux.com/fr03.htm, pp. 1-13, printed Feb. 18, 2003.
Ujang and Vaidya, "Stepped water activity control for efficient interesterification," App. Microbiol. Biotechnol. (1998) 50:318-322.
Chevets, :Use of palm oil on the treatment of wounds, Nigerian Med. K., 9:711-712 (1979).

*Primary Examiner* — Gina C Justice

(74) *Attorney, Agent, or Firm* — Mintz Levin Cohn Ferris Glovsky and Popeo, P.C.; Ivor R. Elrifi; Matthew Pavao

(57) ABSTRACT

A cosmeceutical formulation is provided that includes a mixture of a refined, bleached, deodorized (RBD) palm oils and red palm olein. The resulting formulation is a homogeneous blend with a considerable shelf life. The formulation may be a cream, lotion, sunscreen, or a soap and may be formulated to include additional beneficial oils and EFAs. If a cream formulation is desired, RBD palm stearin is the preferred palm oil for producing a creamy texture. If a lotion is desired, RBD palm oil may be used and chemically modified to produce a tailored oil with a desired melting point and consistency. The formulation may be used to treat a variety of skin conditions including adverse and age-related skin conditions or as an effective moisturizer for the prolonged maintenance of ordinary skin.

35 Claims, 1 Drawing Sheet

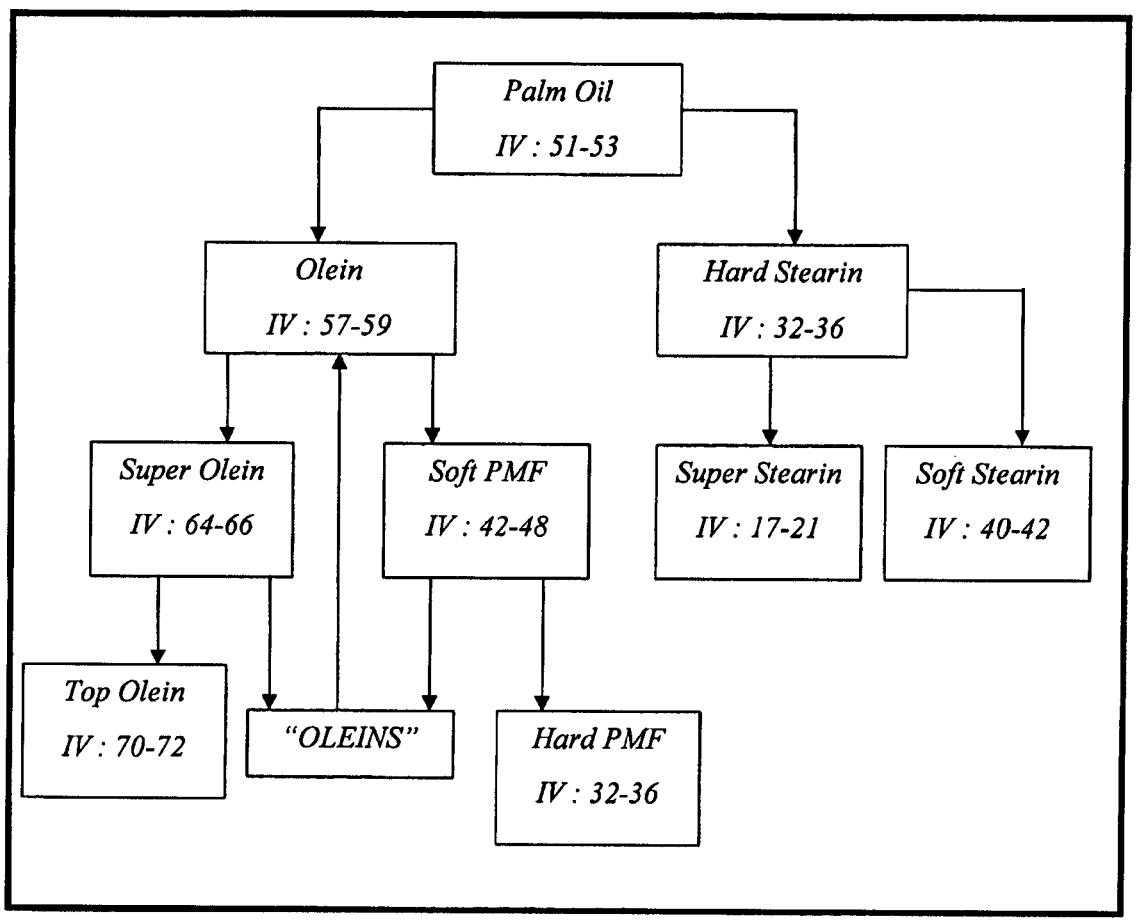

COSMECEUTICAL FORMULATION CONTAINING PALM OILS

CROSS-REFERENCE TO RELATED APPLICATIONS

This application is a continuation and claims the benefit of priority of U.S. patent application Ser. No. 10/855,681, filed May 26, 2004, which pursuant to 35 U.S.C. §119 (e) (1) claims priority to U.S. Provisional Application Ser. No. 60/475,217 filed May 30, 2003; the disclosures of which priority applications are herein incorporated by reference.

FIELD OF THE INVENTION

This invention relates generally to cosmeceutical formulations and methods for improving the appearance, feel, comfort, or biological functioning of the skin. More specifically, the invention relates to cosmeceutical formulations comprising palm oil and red palm olein and its application to the skin for cosmetic reasons and for the treatment of various physical, environmental, and medical skin conditions.

BACKGROUND OF THE INVENTION

As humans age, physical, environmental, and medical conditions affect the quality and appearance of skin. Wrinkles are the most common skin condition associated with physical aging. Dermatologists and plastic surgeons describe two types of wrinkles—static and dynamic. Static wrinkles are wrinkles associated with advancing age; they are caused by the thinning and stretching of the skin over time and are always visible, regardless of whether the facial muscles are active or resting. Dynamic wrinkles are not associated with the aging process; they are temporary wrinkles caused by the creasing of skin and are visible only when the facial muscles are active. Other skin conditions associated with aging are dry skin and liver spots. In addition to aging, dietary swings are another physical condition that affects the quality and appearance of skin. With the stretching of the skin during periods of weight gain and the relaxation of the skin during periods of weight loss, the skin loses its elasticity.

Environmental conditions that affect the skin include exposure to the sun and tobacco smoke. Overexposure to sunlight results in photodamage (also called photoaging), a condition that affects both the epidermal and dermal layers of the skin. Specifically, in the epidermis, photodamage results in the thinning of the epidermal layer of the skin and may also cause the growth of skin lesions, such as actinic keratoses, basal cell carcinomas, and squamous cell carcinomas. In the dermis, photodamage results in an accelerated rate of collagen degeneration resulting in premature aging. With the destruction of the collagen fibers in the dermal layer, sun-induced elastin accumulates in the skin producing large quantities of metalloproteinase enzymes. Normally, metalloproteinases remodel sun-injured skin by manufacturing and reforming collagen; this process does not always work well to repair damaged skin as some metalloproteinases may actually break down collagen. The result of this imperfect repair process is the formation of disorganized collagen fibers known as solar scars. With prolonged and continuous sun exposure, the imperfect rebuilding of the skin by this process results in wrinkles. Exposure to tobacco also has a detrimental effect on the condition of the skin. It has been found that the chemicals inhaled form cigarette smoke constrict the blood vessels in the skin resulting in a diminished flow of oxygen to facial tissues. The reduced flow of oxygen to the facial skin of smokers may result in premature wrinkling and a grayish pallor.

Medical conditions that affect the skin are widespread and include such conditions as acne, acne scarring, rosacea, psoriasis, and eczema. Despite years of research and a myriad of products designed to address these common skin disorders, they remain common conditions that are difficult to cure or to control.

Compositions including vitamins A and E have been touted as effective for the treatment of skin conditions and the reduction in the appearance of wrinkles. The term vitamin A is the generic term to describe the class of fat-soluble compounds known as retinols. The retinols, one of the most active forms of vitamin A, are found in animal foods such as liver and eggs. Retinols, however, are not the only source of vitamin A; the provitamin A carotenoids (also called "carotenoids") found in the darkly colored pigments of some plant foods convert to vitamin A within the body and are thus, another source of vitamin A. The carotenoids are defined by their chemical structure. The majority of carotenoids are derived from a 40-carbon polyene chain, which could be considered the backbone of the molecule. The polyene chain may be terminated by cyclic end-groups and may be complemented with oxygen-containing functional groups. Hydrocarbon carotenoids are known as carotenes. Some common carotenes include beta-carotene, found in carrots; alpha-carotene, found in palm oil; beta-cryptoxanthin, found in red bell peppers and citrus fruits; and lypocene, found primarily in tomatoes. The structure of a particular carotenoid determines the biological function of the pigment. For example, the distinctive pattern of alternating single and double bonds in the polyene backbone of the carotenoids is what allows the compounds to absorb excess energy from other molecules, while the nature of the specific end groups on the carotenoids influences the polarity of the compound. The former may account for the antioxidant properties of biological carotenoids, while the latter may explain the differences in the ways that individual carotenoids interact with biological membranes. Vitamin A and carotenoids play an important role in vision, bone growth, reproduction, cell division, and cell differentiation. These compounds helps to maintain the integrity of skin and mucous membranes and thus, it helps to protect the skin from elements that damage the skin, such as the environmental factors described above, as well as bacteria and viruses, which are the causes of many medical skin conditions, such as those described above. Despite its beneficial effects, the carotenoids have not been successfully used in topical formulations because the pigments of these compounds produce severe skin discoloration.

The term vitamin E is the generic term to describe the class of fat-soluble compounds known as tocols and tocotrienols. The term "tocopherol" is a generic descriptor for all mono-, di-, and trimethyltocols. Alpha-tocopherol is one of the most active tocopherols; it is found in vegetable oils, nuts, and green leafy vegetables. Tocotrienols differ from tocopherols in that the former have an unsaturated isoprenoid side chain. Palm oil is the richest natural source of tocotrienols, and unlike tocopherol, is not found in most of the other vegetable oils such as soybean oil, canola oil, corn oil, and cottonseed oil. Within palm oil, tocotrienols make up about 70% of the total vitamin E in the oil while tocopherols make up only 30% of the total vitamin E in the oil. Both tocopherols and tocotrienols have been found to be powerful biological antioxidant in humans. Antioxidants act to protect cells against the effects of free radicals—those potentially damaging by-products of the body's metabolism that can cause cellular damage. In addition to its anti-oxidant properties, the tocotrienols have been found to be effective at penetrating lipid membranes. The use of tocotrienols for treating or preventing skin damage was disclosed in U.S. Pat. No. 5,545,398 to Perricone.

As a carrier of large quantities of carotenoids, tocopherols, and tocotrienols, palm oil is a desirable vehicle for the delivery of these vitamins to the skin. The use of palm oil in skin care formulations, however, has not been successful because palm oil has a very slow rate of crystallization, which continues even after processing. As a result of the continued crystallization, products containing palm oil products tend towards hardening and therefore, have a very short shelf-life. The problems associated with the crystallization of palm oil products is described in U.S. Pat. No. Re 30,086 to Carlile et al.

SUMMARY OF THE INVENTION

The present inventors have overcome the need in the art for a cosmeceutical formulation containing carotenoids, the tocopherols, and the tocotrienols, by preparing a cosmeceutical formulation made from votated palm oil, palm stearin, and/or palm olein and where appropriate, by using the procedures of structured lipid manufacture to tailor the melting point, consistency, and texture of the formulation. With the formulations described herein, the present inventors have found, surprisingly, that the problems associated with the pigmentation and crystallization of palm oil products is avoided and at the same time, all of the nutritional benefits of palm oil are maintained and even enhanced. Accordingly, the resulting cosmeceutical formulation is a golden-colored cream that is rich in carotenoids, tocopherols, and tocotrienols. The cosmeceutical formulation is unnoticeable upon application, is readily absorbed in the skin, and has a pleasing homogeneous consistency throughout its considerable shelf-life.

In one embodiment of the present invention, there is provided a biocompatible, cosmeceutically acceptable topical formulation comprising a votated blend of a palm oil and red palm olein, wherein the formulation is substantially homogeneous.

In another embodiment of the present invention, there is provided a biocompatible, cosmeceutically acceptable topical formulation comprising a votated blend of: (a) approximately 85 wt. % to 99 wt. % of a RBD palm stearin; (b) approximately 0.5 wt. % to 10 wt. % of red palm super olein; (c) approximately 0.5 wt. % to 5.0 wt. % of additional oil; and optionally (d) approximately 0.5 wt. % to 5.0 wt. % of an individual fatty acid, wherein the formulation is substantially homogeneous, substantially free of crystallized components, and begins to liquefy at a temperature no lower than 80° F.

In a further embodiment of the present invention, there is provided a biocompatible, cosmeceutically acceptable topical formulation comprising a votated blend of: (a) approximately 85 wt. % to 99 wt. % of a RBD palm oil; (b) approximately 0.5 wt. % to 10 wt. % of red palm super olein; (c) approximately 0.5 wt. % to 5.0 wt. % of additional oil; and optionally (d) approximately 0.5 wt. % to 5.0 wt. % of an individual fatty acid, wherein the formulation is substantially homogeneous, substantially free of crystallized components, and begins to liquefy at a temperature no lower than 80° F.

In yet another embodiment of the present invention, there is provided a biocompatible, cosmeceutically acceptable topical formulation comprising a votated blend of: (a) approximately 50 wt. % to 75 wt. % of an RBD palm oil; (b) approximately 24 wt. % to 35 wt. % of RBD palm stearin; (c) approximately 0.5 wt. % to 10 wt. % of a red palm olein; (d) approximately 0.5 wt. % to 5.0 wt. % of additional oil; and optionally (e) approximately 0.5 wt. % to 5.0 wt. % of an individual fatty acid, wherein the formulation is substantially homogeneous, substantially free of crystallized components, and begins to liquefy at a temperature no lower than 80° F.

The foregoing formulations may be topically applied to the skin of an individual for delivery of a carotenoid to the skin or for treating a variety of skin conditions including adverse and age-related skin conditions or as an effective moisturizer for prolonged maintenance of ordinary skin.

BRIEF DESCRIPTION OF THE DRAWINGS

FIG. 1 is schematic diagram of the by-products of palm oil fractionation.

DETAILED DESCRIPTION OF THE INVENTION

Definitions and Nomenclature

Unless otherwise indicated, the invention is not limited to specific manufacturing processes, components, or uses, as such may vary. It is also to be understood that the terminology used herein is for the purpose of describing particular embodiments only, and is not intended to be limiting.

As used in this specification and the appended claims, the singular forms "a," "an," and "the" include plural referents unless the context clearly dictates otherwise. Thus, for example, "an additional oil" refers not only to a single additional oil but also to two or more additional oils, typically in admixture, reference to "a red palm olein" includes a single such olein (e.g., red palm super olein) or to a mixture of two or more such oleins (e.g., red palm super olein and red palm top olein), and the like.

In describing and claiming the present invention, the following terminology will be used in accordance with the definitions set out below.

The terms "treating" and "treatment" as used herein refer to reduction in severity and/or elimination of a skin condition, whether a localized and temporary condition (e.g., sunburn), a manifestation of a minor systemic infection (e.g., chicken pox), or the result of a serious and ongoing systemic disorder (e.g., a rash associated with systemic lupus erythematosis). The term "treating" also refers to the prevention of a skin condition, including, but not limited to, prevention of an adverse skin condition in individuals who have already been treated for the skin condition or likely to develop the condition.

By a "cosmeceutically effective" formulation or component is meant a nontoxic formulation or component that may or may not have medicinal or drug-like properties, but which, when applied to the skin, beneficially affects the appearance, feel, comfort, and/or biological functioning of the region of the skin to which the formulation or component is applied.

The term "cosmeceutically acceptable" refers to a formulation or component that is topically administrable without causing any significant undesirable effects or interacting in a deleterious manner with any of the other components of the cosmeceutical formulation in which it is contained. The term "topical application" is used in its conventional sense to mean the application of a formulation to the skin surface.

The term "synthetic" refers to a non-naturally occurring compound or composition that can be prepared by chemical synthesis. Naturally occurring compounds and compositions that have been chemically synthesized are not "synthetic" as that term is used herein.

The terms "substantially homogeneous," "substantially water-free," and the like, refer to compounds or compositions that are at least 90 wt. %, preferably at least 95 wt. %, and optimally at least 99 wt. % homogeneous, water-free, etc.

The terms "water-free," "moisture-free," and the like, refer to compounds or compositions that contain no water, moisture, etc.

The term "homogeneous" refers to a consistency that is uniform throughout.

The term "votating" refers the procedures by which oil is passed through a heat exchanger and is rapidly chilled until it is supercooled. The resulting crystallized product is extruded to form a creamy and homogeneous blend.

The term "interesterification" refers to a process for changing the physical and functional properties of oils or fats by rearranging the natural distribution of fatty acids in glycerides. Interesterification is a catalytic process that is carried out at relatively low temperatures.

The term "hydrogenation" refers to the process by which oil is hardened by saturating the ethylene bonds of the triacylglyceride (TAG) molecules. Hydrogenation can be partial or full and is used to alter the melting points, rate of crystallization, and oxidative stability of liquid oil products.

By application on an "as-needed" basis is meant that the formulation is not applied within the context of an ongoing or regular regimen.

"Carriers" or "vehicles" as used herein refer to carrier materials suitable for incorporation in a topically applied composition. Carriers and vehicles useful herein include any such materials known in the art, which are nontoxic and do not interact with other components of the formulation in which it is contained in a deleterious manner.

"Optional" or "optionally" means that the subsequently described circumstance may or may not occur, so that the description includes instances where the circumstance occurs and instances where it does not. For example, an additional component that is indicated as "optional" or "optionally present" means that the additional component may or may not be present in a given formulation, and, thus, the description includes formulations in which the additional component is present and formulations in which it is not.

Formulations, Manufacture, and Use

I. The Fundamental Components

Palm Oils and Palm Oleins

Palm oil is a generic term that includes a family of palm oils including raw or crude palm oil, processed palm oil, and chemically modified palm oil. When palm oil is fractionated, it separates into palm olein, which is a liquid, and palm stearin, which is a solid. The formulation of the present invention is made by unique combinations of palm oil, palm olein, and palm stearin.

A. Crude Palm Oil

Crude palm oil is derived from the mesocarp of the oil palm fruit. The oil palm fruit is a drupe, which is comprised of three layers: the exocarp (the skin), the mesocarp (the outer pulp containing palm oil), and the endocarp (a hard shell enclosing the kernel, which contains oil and carbohydrate reserves for the embryo). The crude palm oil from the mesocarp has physical and chemical properties that are distinct from the oil obtained form the kernel (the endosperm).

Extraction of crude palm oil from the oil palm fruit is most efficiently accomplished by way of double pressing. Under the double-pressing technique, the first press and the second press are carried out at different temperatures with the first pressing carried out at a lower temperature in order to avoid cracking the nut. After the first press, the endocarp is removed and the mesocarp is subjected to the second press. Advantages of the double pressing over the conventional single pressing technique are a lower loss of oil in the fiber, a higher kernel extraction rate, and reduction of contamination of the crude palm oil with kernel oil.

Like all oils, TAGs are the major component of palm oil, accounting for 95% of palm oil. TAGs are glycerol molecules esterified with three fatty acids as follows:

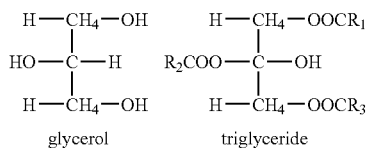

wherein $R_1$, $R_2$, and $R_3$ are hydrocarbon chains, which may vary in both chain length and saturation or unsaturation of carbon-to-carbon bonds. It is the variations in $R_1$, $R_2$, and $R_3$ that define the chemical and physical properties of oils and fats, such as the melting point and crystallization behavior of the oil.

For crude palm oil, the chain length of the fatty acids present in the TAGs falls within a very narrow range from twelve to twenty carbons. Generally, the longer the chain length, the higher the melting point of the fatty acid. Accordingly, arachidic acid, with a chain length of 20 has a higher melting point than lauric acid. The melting point of palm oil is in the range of 28-31° C.

The fatty acid content in crude palm oil is approximately 50% saturated, 40% monounsaturated, and 10% polyunsaturated. Generally, the more unsaturated the fatty acid, the more unstable it will be. The degree of saturation or unsaturation and the fatty acid chain length both have effects on the functional and physical characteristics of palm oil. Specifically, saturated fatty acids have single carbon-to-carbon bonds are very stable. Examples of saturated fatty acids are palmitic acid (C16:0) and stearic acid (18:0). Unsaturated fatty acids have carbon-to-carbon double bonds. Generally, the more unsaturated the fatty acid is, the more unstable it is. Monounsaturated fatty acids have one double bond, e.g., oleic acid (C18:1) and polyunsaturated fatty acids have more than one, e.g., linoleic acid is diunsaturated with two carbon-to-carbon double bonds (C18:2) and linolenic acid is triunsaturated with three carbon-to-carbon double bonds (C18:3). Table 1 shows the chain length, saturation or unsaturation, and percentage of the fatty acids in Malaysian Crude Palm Oil.

TABLE 1

FATTY ACID COMPOSITION OF MALAYSIAN CRUDE PALM OIL

| FATTY ACID | | % OF TOTAL ACIDS | |
|---|---|---|---|
| CHAIN LENGTHS | NAME | MEAN | RANGE |
| C12:0 | Lauric Acid | 0.23 | 0.1-1.0 |
| C14:0 | Myristic Acid | 1.09 | 0.9-1.5 |
| C16:0 | Palmitic Acid | 44.02 | 41.8-46.8 |
| C16:1 | Palmitoleic Acid | 0.12 | 0.1-0.3 |
| C18:0 | Stearic Acid | 4.54 | 4.2-5.1 |
| C18:1 | Oleic Acid | 39.15 | 37.3-40.8 |
| C18:2 | Linoleic Acid | 10.12 | 9.1-11.0 |
| C18:3 | Linolenic Acid | 0.37 | <0.05-0.6 |
| C20:0 | Arachidic Acid | 0.38 | 0.2-0.7 |

The remaining glyceridic material consists primarily of monoacylglycerides and diacylglycerides, referred to collectively as "partial glycerides," and free fatty acids (FFAs). Oil obtained from unbruised fruit generally shows trace levels of partial glycerides; however, larger amounts of partial glycerides are seen in bruised and overripe palm fruit as a result of the partial hydrolysis of the TAGs in the damaged and aging fruit. Because it is known that the presence of partial glycerides affects the crystallization behavior of oils, it is important to select unbruised fruit when preparing crude palm oil.

In addition to glyceridic components, crude palm oil also contains approximately 1% of minor non-glyceridic components including carotenoids (vitamin A precursors) and chlorophyll pigments, tocopherols and tocotrienols (vitamin E components), sterols, phospholipids, glycolipids, and terpenic and aliphatic hydrocarbons. These minor components are often referred to as the "unsaponifiable components" of palm oil.

The pigmentation of palm fruits is related to its stage of maturity. Two classes of natural pigments occur in crude palm oil: carotenoids and chlorophyll. Palm oil from young fruits contains more chlorophyll than carotenoids while palm oil from ripe fruits tends to be carotenoid-rich, with the high levels of carotenoids visually masking the presence of chlorophylls. The presence of the carotenoids in palm oil gives the oil a rich orange-red color. Because the use of a rich orange-red oil is not desirable in the food or cosmetic industries, palm oil has traditionally been processed in order to remove the dark pigmentation of the oil and produce a more visually pleasing light yellow to golden colored oil. The disadvantage of the processing of crude red palm oil is that the resulting oil is depleted of many of its nutritionally rich components, including the carotenoid pigments.

Palm oil may be refined chemically or physically. The two methods differ in the way the free fatty acids (FFAs) are removed from the oil. Chemical refining uses an alkali to neutralize most of the fatty acids, which are removed as soap. Physical refining uses steam distillation under a vacuum at high temperatures to remove the FFAs. Physical refining has the advantage of not producing a soap and therefore, an effluent plant to remove soap stock is not required in physical refining. Crude palm oil that is manufactured by way of chemical refining is known as NBD (neutralized, bleached, deodorized) palm oil, while crude palm oil that is manufactured by way of physical refining is known as RBD (refined, bleached, deodorized) palm oil. Despite the difference in manufacturing between the chemical and physical refining processes, there is very little difference between the qualities of the NBD and RBD palm oil produced by the two refining procedures.

In both chemical and physical refining, crude palm oil is prepared for processing by degumming the crude palm oil with phosphoric acid. The degumming pretreatment step begins by heating the crude palm oil at a steady rate up to 45° C., the temperature at which the oil is easily pumped; keeping the crude oil homogenized to provide final product consistency; and gum conditioning the crude oil. With gum conditioning, the temperature of the crude oil is raised to approximately 80° C. by pumping the crude oil through a heat exchanger and then treating the heated oil with 0.05%-0.10% high grade orthophosphoric acid in a mixer. After a reaction time of approximately 15 minutes, the gums (phosphatides) precipitate-out of the oil mixture and are easily removed. Once this pretreatment is complete, the crude oil may be chemical or physically refined.

B. NBD Palm Oil

The first step in the manufacture of chemically refined NBD palm oil products is neutralization, which serves to reduce the FFA content in the crude palm oil product. In this step, the orthophosphoric-acid-treated crude palm oil is dosed with caustic soda; the concentration and amount of the alkali will vary depending on the FFA content of the oil. The formulation is then mixed so that the alkali reacts with the FFAs forming precipitated soaps, which are removed through either centrifugation or settling and washing. Both separation procedures will yield two phases: a light phase discharge, which is mainly refined oil containing trace amounts of soap and moisture, and a heavy phase discharge, which is primarily soap, insoluble materials, gums, free alkali and minute quantities of neutralized oil. At this separation stage, a certain amount of neutral oil is saponified along with the FFA and is lost by emulsification. The efficiency of the process can be determined by way of a refining factor (RF) as follows:

$$RF = \frac{\text{Oil loss \%}}{FFA}$$

The neutralized oil is then washed with water to remove the soap and other impurities and the resulting oil-water mixture is passed through a centrifuge separator to separate the heavy and light phase discharges. The centrifuged light phase discharge should have a soap content less than 80 ppm, which will be removed at the next bleaching step. After centrifugation, the light phase discharge is dried in a vacuum dryer; the resulting oil is a semi-refined palm oil called neutralized palm oil (NPO). As a semi-refined product, NPO still retains many undesirable impurities, odors, and pigments, many of which are removed through bleaching.

The second step in the manufacture of NBD palm oil products is bleaching, which serves to remove impurities from the oil product through adsorption. In this step, activated clay, i.e., bleaching earth, is added to the NPO to remove undesirable impurities and improve the oxidative stability of the oil; adsorb soap traces, pro-oxidant metal ions, and other impurities; and decompose peroxides. Bleaching is carried out under a vacuum at a temperature of about 100° C. for 30 minutes. The dosage of bleaching earth added to the NPO varies with the type and quantity of starting oil and is usually in the range of 0.5%-1.0%. The slurry containing the bleaching earth is then passed through a system of filters to yield a clear oil called neutralized, bleached (NB) palm oil. Although the pigmentation of NB palm oil is somewhat reduced as a result of the bleaching process, the vast majority of the color reduction of palm oil products is achieved through deodorization.

The third step in the manufacture of NBD palm oil is deodorization, which serves to further reduce the FFA content and destroy the chromogenic properties of the carotenoids. Deodorization is a high temperature, high vacuum, steam distillation process, which operates by subjecting the oil to de-aeration, heating, stripping, and cooling. Deodorization can be carried out in batch, continuous, or semi-continuous style. In continuous alkali refining, the oil is generally heated 220° C.-240° C. under a vacuum of 2-5 mbar. At this temperature, the carotenoid pigments are thermally destroyed. The use of direct stripping steam in the deodorization system removes residual FFAs, aldehydes, and ketones, which are responsible for the undesirable odors and flavors of crude and semi-refined palm oil products. When the palm oil product leaves the deodorizer it remains under a vacuum until it has been cooled to a temperature below 60° C. Once it has reached its target temperature, the palm oil product passed through polishing filter and is sent to a storage tank as NBD palm oil, a light yellow stable product with a bland flavor.

C. RBD Palm Oil

As mentioned above, RBD palm oil is crude palm oil that is physically refined. The manufacture of RBD palm oil is similar to that of NBD palm oil, with the exception of the neutralization step. Accordingly, the crude palm oil is pre-treated with phosphoric acid as described above. After pretreatment, the degummed crude oil product is directly subjected to bleaching. With physical refining, higher doses of earth are used than with chemical refining. The excess earth adsorbs impurities, which are removed with soapstock and washing as in the chemical refining process. The pre-treated oil then enters the deodorizer with an FFA content that is much higher than the FFA content of NB oil. In light of the higher FFA content, the deodorization is carried out at a higher temperature than for chemical refining and requires more stripping steam and a larger vacuum. The temperature required for physical refining is in the range of 250° C.-270° C. The oil leaves the deodorizer as RBD oil.

For the cosmeceutical formulations of the present invention, RBD palm oil and RBD palm stearin are the preferred processed palm oil products D. Palm Oleins and Palm Stearins As a result of fully saturated triglycerides and high melting point mono-oleoglycerides, crude palm oil exists as a semi-solid fat at ordinary room temperature; accordingly, it must be subjected to fractionation in order to reduce it to liquid form. The solid nature of the crude palm oil is due to the presence of solid, fully saturated TAGs and high melting point mono-oleoglycerides and monolinologlycerides.

Fractionation of palm oil results in two by-products: 20-30% solid fat, called palm stearin, and 70%-80% liquid oil, called palm olein. There are three types of fractionation: dry fractionation, detergent fractionation and solvent fractionation. All three processes involve the gradual lowering of the temperature of the palm oil to induce crystallization and the consequent separation of the higher melting point triglycerides (the solid stearin) from the lower melting point triglycerides (the liquid olein).

With dry fractionation, the palm oil is preheated to approximately 70° C. to destroy any crystals that may be present in the oil. The oil is then gradually cooled under agitation. The resulting slurry is filtered to separate the solid stearin from the liquid olein.

With detergent fractionation, a detergent, such as sodium lauryl sulphate, and an electrolyte, such as magnesium sulphate, are used to crystallize the oil and separate the fractions. The electrolyte agglomerates the oil droplets formed during the mixing process while the detergent fractionates and wets the stearin crystals and displaces occluded and entrained olein. The lower density olein is then separated from the higher density stearin-detergent mixture through centrifugation. Traces of detergent in the olein fraction may be removed by washing. The heavier stearin phase containing most of the detergent is heated to melt the stearin and then centrifuged to separate the stearin from the detergent. The isolated detergent may be recycled.

With solvent fractionation, a solvent such as hexane or acetone is used to crystallize the fractions. The fractions may be selectively crystallized at different temperatures, with the cooling carried out by either chilled water or brine, the latter used if very low temperatures are desired. The olein and stearin fractions are separated from the solvent by way of filtration.

Further fractionation of the olein component yields double fractionated olein, referred to as "super olein," and a "palm mid-fraction" (PMF). Palm super olein has a higher Iodine Value (IV) and consequently, a lower cloud point than single fractionated palm olein. The IV value is used to measure the content of unsaturation or double bonds capable of reacting with iodine; it is defined as the percentage of iodine absorbed by the oil or fat under test conditions. Methods for IV determination are known to those of ordinary skill in the art and include the Wijs and Hanus methods. Cloud point measures the resistance of an oil to crystallization; it is generally used as one of the specifications for palm olein. The cloud point test includes cooling the olein until it begins to cloud as a result of crystal formation. A high IV value is usually indicative of a low cloud point, i.e., a liquid oil, while a low IV value usually indicates that the oil is in the form of a solid. If palm oil is subjected to triple fractionation, the resulting product is referred to as "super top olein." The fractionation of crude palm oil is diagrammed schematically in FIG. 1 and includes the IV ranges for each fraction.

The stearin that is originally fractionated from palm oil is hard and consequently is often referred to as "hard stearin." Further fractionation of hard stearin results in "super stearin" and "soft stearin"; with the soft stearin having a higher IV value than the super stearin.

Since fractionation does not destroy the carotenoids and other unsaponifiable nutrients found in crude palm oil, both palm stearin and palm olein maintain the rich orange-red color of the crude oil upon fractionation. Accordingly, the palm olein and palm stearin products discussed herein are often referred to as red palm olein, red palm super olein, red palm top olein, red palm stearin, red palm super stearin, and red palm soft stearin. In this same vein, NBD and RBD palm oil that are subjected to fractionation result in NBD and RBD palm oleins and NBD and RBD palm stearins. As with the NBD and RBD palm oils, NBD and RBD palm oleins and stearins are void of the pigments found in the crude oil products.

As the majority of the fatty acids and nutrients filter into the liquid fraction, palm olein generally has a higher percentage of fatty acids and nutrients than does palm stearin. Because small amounts of liquid oil may remain in stearin after fractionation, the solid fat is often subjected to "pressing" following fractionation. With pressing, liquid oil is pressed out of the solid fat by means of hydraulic pressure. The process produces a harder solid fat with no extra liquid.

Table 2 shows the fatty acid composition of crude palm oil, palm olein, palm super olein, and palm stearin.

TABLE 2

FATTY ACID COMPOSITION OF PALM OIL PRODUCTS

| FATTY ACID CHAIN LENGTHS | NAME | CRUDE PALM OIL | PALM OLEIN | PALM SUPER OLEIN | PALM STEARIN |
|---|---|---|---|---|---|
| C12:0 | Lauric Acid | 0.23 | 0.3 | 0.4 | 0.25 |
| C14:0 | Myristic Acid | 1.09 | 1.0 | 1.1 | 1.45 |
| C16:0 | Palmitic Acid | 44.02 | 39.8 | 31.5 | 62.2 |
| C16:1 | Palmitoleic Acid | 0.12 | 0.2 | — | 0.07 |
| C18:0 | Stearic Acid | 4.54 | 4.4 | 3.2 | 5.0 |
| C18:1 | Oleic Acid | 39.15 | 42.2 | 49.2 | 24.8 |
| C18:2 | Linoleic Acid | 10.12 | 11.2 | 13.7 | 5.9 |
| C18:3 | Linolenic Acid | 0.37 | 0.4 | 0.3 | 0.3 |
| C20:0 | Arachidic Acid | 0.38 | 0.4 | 0.4 | 0.45 |

E. Chemical Modification of Palm Oil Products

The structured lipids of the present invention are achieved by chemically modifying the palm oil products discussed herein. Structured lipids refer generally to tailor-made oils and fats that have improved nutritional or physical properties as a result of modifications to the fatty acids on the glycerol backbone of the TAG molecules. Such modifications may include the incorporation of new fatty acids on the glycerol backbone or more commonly, changes in the position of existing fatty acids on the glycerol backbone.

Chemical modification of a palm oil product generally affects the oil's melting point and rate of crystallization, and consequently, alters the consistency or texture of the resulting product. Because TAGs constitute 95% of palm oil, the chemical modification of palm oil products is dominated by ester group reactions. Generally, palm oil products are chemically modified using the procedures of interesterification (including partial or complete acidolysis, alcoholyis, and transesterification) and hydrogenation (including partial or complete alkoxylation, ethoxylation, and propoxylation). For processed NBD and RBD palm oil, the chemical modification is generally carried out between the bleaching and deodorization steps.

1. Interesterification

The group of reactions in which an ester of a fatty acid is reacted with fatty acid, alcohols, or other fatty acid esters is broadly termed "interesterification." Interesterification reactions involve the rearrangement or redistribution of fatty acids attached to the glycerol part of the TAG molecule. The rearrangement can be either random or direct depending on the processing conditions. Interesterification reactions fall into one of the following three categories: (i) acidolysis, a reaction of fatty esters with an acid (usually a fatty acid) where acyl moiety is displaced between an acyl glycerol and a carboxylic acid; (ii) alcoholysis, a reaction between a fatty acid ester and an alcohol where an acyl moiety is displaced between an acyl glycerol and an alcohol; and (iii) transesterification, an exchange of acid radicals from one fatty acid ester to another where two acyl moieties are exchanged between two acylglycerols. With each of these reactions, hydrolysis and esterification occur simultaneously; with the hydrolysis reaction serving to cleave the acyl bonds and the esterification serving to form the new acyl bonds.

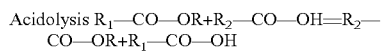

Acidolysis $R_1$—CO—$OR+R_2$—CO—OH=$R_2$—CO—$OR+R_1$—CO—OH

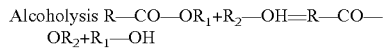

Alcoholysis R—CO—$OR_1$+$R_2$—OH=R—CO—$OR_2$+$R_1$—OH

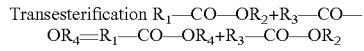

Transesterification $R_1$—CO—$OR_2$+$R_3$—CO—$OR_4$=$R_1$—CO—$OR_4$+$R_3$—CO—$OR_2$ Interesterification reactions are reversible and allow for modification of the physical properties of fats, such as melting point, crystallization, solid fat content, and plasticity, while retaining the chemical and nutritional properties of the fats. By using interesterification, crude and processed palm oil products can be made more homogeneous.

When carried out in the presence of catalysts, interesterification reactions can be carried out at relatively low temperatures; otherwise, high temperatures are required in order for the reactions to proceed. The most commonly used catalysts for interesterification reactions are metal alkylates, such as sodium methylate, sodium ethylate, sodium metal, sodium/potassium alloy, and the hydroxide of sodium and potassium in combination with glycerol, although lipase-catalyzed reactions are also used. An example of a lipase-catalyzed transesterification reaction is the use of immobilized *Rhizomucor meihei* lipase to replace the palmitic oil in palm oil with stearic acid. R. Sharma et al. (2001), "Production, Purification, Characterization, and Applications of Lipases," *Biotechnology Advances*, 19:627-662, 631. A combination of chemical and lipase catalyzed reactions may also be used to interesterify palm oil products. H. T. Osborn and C. C. Akoh (2002), "Structured Lipids—Novel Fats with Medical, Nutraceutical, and Food Applications" *Comprehensive Reviews in Food Science and Food Safety*, 3:93-104, 94. Because interesterification reactions require water to run the hydrolysis reaction and a lack of water to run the esterification reaction, the reactions are best performed in a reactor with a water activity step change. It is important that the presence of water in the esterification stage be at an absolute minimum since the presence of excess water may cause the hydrolysis reaction to dominate resulting in the accumulation of glycerol, FFAs, and partial glycerides.

2. Hydrogenation

Hydrogenation of oils, also referred to as "hardening," is an addition reaction involving saturation of the ethylene bonds of a TAG with hydrogen. Hydrogenation can be full or partial and in both cases requires a catalyst to speed the reaction. Upon full hydrogenation, all of the double bonds of the TAG are eliminated and the product is reduced to a hard brittle solid at room temperature. Accordingly, with respect to palm oil products, partial hydrogenation, preferably <10% by weight is preferred. Partial hydrogenation of palm oil may result in the following: (i) a change from the cis form to the trans form of unsaturated bonds (geometric isomerization); (ii) a change in the position of the unsaturated bonds (positional isomerization); and (iii) formation of conjugated systems of unsaturated bonds in polyunsaturated fatty acid side chains (conjugation). The formation of trans double bonds, however, is dependent on the catalytic material used and the hydrogenation conditions, e.g., temperature, pressure, and stirring rate. For example, nickel-sulfur catalysts lead to the formation of more trans isomers than conventional nickel catalysts while low temperature hydrogenation with more active precious metals can limit the formation of trans isomers. For example, palm oil can be hydrogenated with used nickel catalyst or a sulphur-poisoned catalyst to increase its solid fat content (SFC) at 10° C. without a significant increase in its melting point; however, generally, the progression of the hydrogenation reaction results in a gradual increase of the melting point of the oil or fat. Accordingly, hydrogenation is the process most commonly used to alter the melting point, and rate of crystallization of liquid oil products. Hydrogenation has the end result of enhancing the oxidative stability of the oil products.

Once a palm oil product has been hydrogenated, it may be alkoxylated in order to increase the water solubility of the palm oil product. In the alkoxylation process, an ethylene oxide (ethoxylation) or a propylene oxide (propoxylation) are reacted with the TAGs to form a smooth cream with improved moisturizing properties. Alkoxylated palm oil product may be used to produce soap-based products in addition to moisturizers. In the production of soaps, it is preferred to alkoxylate the TAGs after saponification when the oil product is already in a hardened rather than a liquid state. The degree of alkoxylation, i.e., partial or total, will vary with the desired end product. For example, a lower degree of alkoxylation will be needed to produce a moisturizer than a hard soap, the latter required a higher degree of alkoxylation. U.S. Pat. No. 6,544,938 to Yaravoy et al. describes soap products with alkoxylated triglycerides. Soaps and cosmetic compositions prepared using ethoxylated and propoxylated esters are described in European Patent Application No. EP 1221 313.

The end products of hydrogenation-ethoxylation and hydrogenation-propoxylation reactions are fully saturated functional replacements for palm oil and acceptable starting materials for cosmeceutical formulations. For example, hydrogenated-ethoxylated palm oil products have been found to be useful as emulsifiers, wetting agents, dispersants, superfatting agents, emollients, and plasticers and hydrogenated-propoxylated palm oil products are useful as emollients and skin lubricants.

3. Hydrolyzation and Saponification

To ensure that the palm oil products used in the claimed cosmeceutical formulation are of the highest quality, it is important that the palm fruit and the resulting palm oil products have not become hydrolyzed. Accordingly, the preparation of the claimed formulations should be at least substantially water-free and preferably completely water-free. Hydrolysis of the palm fruit and of palm oil products can be in the form of microbial lipolysis, autocatalytic hydrolysis, or enzymatic lipolysis. Microbial lipolysis occurs when microorganisms enter the palm fruit and liberate the lipase enzyme. Improper storage of fruits and delayed processing favor the multiplication of microorganisms and hydrolysis of the resulting palm oil. Autocatalytic hydrolysis of palm oil occurs in the presence of water. The rate of the hydrolytic reaction depends on the temperature, moisture content, and initial FFA concentration of the palm oil product. Enzymatic lipolysis occurs when endogenous lipase is released in the palm fruits. Bruised fruits display more lipolytic activity than undamaged fruits. Over-ripe fruits, processing delay, and rough handling of palm fruit bunches all contribute to palm oil acidification. Accordingly, good harvesting and handling are essential to avoid enzymatic lipolysis.

During the processing of NBD and RBD palm oil products, it is important that the saponification of the palm oil products is kept to a minimum for both environmental and economical reasons. Saponification, or alkaline hydrolysis of an organic ester, produces an alkaline salt and alcohol. When a TAG is treated with alkali, it yields the salt of the alkali metal (soap) and glycerol. This is the basic reaction in the making of soap and glycerin from palm oil. Despite the foregoing, saponification has an important role during the refining process, namely it is important in order to determine the acidity and saponification number of the resulting fats and oils. The saponification number indicates the average molecular weight or equivalent weight of fatty materials in the oil and is therefore, an important identify characteristic of an oil or fat. Palm oil has a saponification number, or value, between 192 and 205. Saponification is represented by the following chemical reaction:

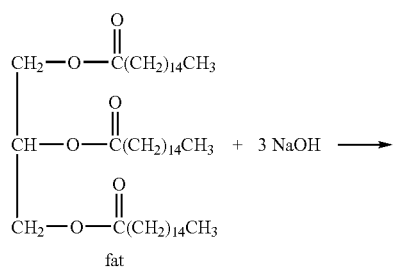
fat

-continued
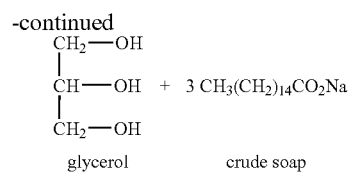
glycerol      crude soap

When preparing the cosmeceutical formulation of the present invention, each of the palm oil products discussed herein may be interesterified, hydrogenated, and/or alkoxylated as appropriate in order to produce an end-product with an appropriate melting point, consistency, and texture for its intended use. For example, a skin lotion will may support a lower melting point and a softer consistency and a smoother texture than will a cream, which will require a higher melting point, a harder consistency, and a stiffer texture.

F. Palm Oil Components

The even balance between the saturated and unsaturated fatty acids in crude palm oil determines the IV of the oil (about 52, which is indicative of a semi-solid state) and confers oxidative stability to the oil, in comparison with other vegetable oils.

As shown in Table 2, the major fatty acids in palm oil are palmitic acid, stearic acid, oleic acid, and linoleic acid. As shown in Table 3, these four fatty acids are part of the Essential Fatty Acids (EFAs), which form part of the lipid complex of the epidermis and aid skin barrier function by helping to control transepidermal water loss. Table 3 shows the EFA profile for human skin lipids.

TABLE 3

EFA PROFILE FOR HUMAN SKIN

| FATTY ACID | CONCENTRATION IN SKIN LIPIDS (%) |
|---|---|
| Palmitic Acid | 30.0 |
| Palmitoleic Acid | 8.0 |
| Stearic Acid | 13.0 |
| Oleic Acid | 17.0 |
| Linoleic Acid | 14.0 |

Because human skin is low in EFAs, it is prone to transepidermal water loss and the dry skin associated with the water loss. Accordingly, the presence of high amounts of EFAs in palm oil has the benefit of reducing transepidermal water loss and preventing the dry skin. Unsaturation of linoleic acid results in α- and γ-linolenic acids, fatty acids with anti-inflammatory properties that have been shown improve the appearance of sun-damaged and aging skin.

1. The Unsaponifiable Matter

Because the unsaponifiable matter of palm oil is rich in anti-oxidants, additional oxidation of palm oil and its fractions is not necessary. The oxidative protection derived from crude palm oil and its fractions is primarily due to the presence of the carotenoids, tocotrienols, and tocopherols, with the other components having lesser anti-oxidant effects.

Carotenoids are the precursors to vitamin A; they are unsaturated tetraterpene molecules biosynthesized from eight isoprene units, the majority of which are all-trans. Carotenoids are divided into two main classes: carotenes and xanthophylls. Carotenes are strictly polyene hydrocarbons. Alpha and beta-carotene are the major carotenoids in palm oil accounting for 90% of the total carotenoids therein, with β-carotene having the highest provitamin A activity. In crude palm oil, the carotenoids offer oxidative protection by undergoing oxidation prior to the TAGs. Table 4 sets forth the carotene concentrations present in Malaysian Crude Palm Oil.

TABLE 4

CAROTENE COMPOSITION OF MALAYSIAN CRUDE PALM OIL

| CAROTENE (PPM) | PERCENTAGE |
|---|---|
| Phytoene | 1.27 |
| cis-β-Carotene | 0.68 |
| Phytofluene | 0.06 |
| B-Carotene | 56.02 |
| A-Carotene | 35.16 |
| cis-α-Carotene | 2.49 |
| Z-Carotene | 0.69 |
| γ-Carotene | 0.33 |
| Δ-Carotene | 0.83 |
| Neurosporene | 0.29 |
| β-Zeacarotene | 0.74 |
| α-Zeacarotene | 0.23 |
| Lycopene | 1.30 |
| TOTAL CAROTENE | 673 |

Xanthophylls are oxygenated carotenes; the oxygenation of these compounds may be in the form of hydroxy (e.g., zeaxanthin and lutein), keto, epoxy, or carboxyl groups.

Although carotenoids represent less than 1% of the components in crude palm oil, after extraction and fractionation, the concentration of carotenoids in crude palm oil far exceeds the concentration of carotenoids found in other vegetable oils. For example, corn oil, groundnut oil, soy-bean oil, rapeseed oil, linseed oil, olive oil, barley oil, sunflower oil, and cottonseed oil, all have concentrations of carotenoids that are in the range of 100 ppm or less. By contrast, crude palm oil has a high carotenoid content (630-700 ppm), which imparts the oil's orange-red color. The concentration of carotenoids in various palm oil fractions is set forth in Table 5.

TABLE 5

CAROTENOID CONTENT OF VARIOUS PALM OIL FRACTIONS

| PALM OIL FRACTION | PPM |
|---|---|
| Crude palm oil | 630-700 |
| palm olein | 680-760 |
| palm stearin | 280-540 |
| Residual oil from palm fruit fiber | 4,000-6,000 |
| Oil from palm leaves | ~1,900 |
| Second-pressed oil | 1,800-2,400 |

Total carotenoids estimated at 446 nm as ppm of β-carotene

Although high concentrations of carotenoids may be obtained from the pressed fiber of the palm fruit (and from palm leaves), these carotenoids have a different chemical composition from the carotenoids found in crude palm oil, crude palm olein, and crude palm stearin. For example, the α- and β-carotenes in the fiber oil only constitute about 50% of the total carotenoids, with phytoene, lycopene, γ-carotene, and δ-carotene present at higher concentrations than they are in crude palm oil. The carotenoid profile of the second-pressed oil is similar to that of the fiber oil.

Because the carotenoids are thermally destroyed during the deodorization stage of the refining process, carotenoids are usually extracted from crude palm oil prior to refining.

Vitamin E is a fat-soluble vitamin, which is comprised of two major homologous series of compounds: the tocopherols and tocotrienols, referred to collectively as "tocochromanols." The tocopherols are structurally characterized by a saturated side chain in the chroman ring and the tocotrienols are structurally characterized by an unsaturated phytyl side chain. Four homologs of each of the tocopherols and the tocotrienols are known with each having differing degrees of antioxidant and vitamin E activity. Tocopherols are predominantly found in vegetable oils, especially seed oils, while tocotrienols are predominantly found in palm oil and cereal oils, such as barley and rice bran oils.

The vitamin E content in crude palm oil ranges between 600-1000 ppm and is a mixture of 78-82% tocotrienols and 18-22% tocopherols. The major tocochromanols in palm oil are α-tocopherol, γ-tocotrienol, and δ-tocotrienol. The concentration of each of the tocopherols and tocotrienols in crude palm oil is set forth in Table 6.

TABLE 6

TOCOPHEROLS AND TOCOTRIENOLS IN CRUDE PALM OIL

| TYPE | PERCENTAGE |
|---|---|
| α-tocopherols | 21.5 |
| β-tocopherols | 3.7 |
| γ-tocopherols | 3.2 |
| δ-tocopherols | 1.6 |
| α-tocotrienols | 7.3 |
| β-tocotrienols | 7.3 |
| γ-tocotrienols | 43.7 |
| δ-tocotrienols | 11.7 |

The vitamin E content of palm oil is partially lost as a result of processing and fractionation. For example, it has been reported that RBD palm oil, RBD palm olein, and RBD palm stearin retain approximately 69%, 72%, and 76% of the original level of vitamin E found in the crude oils, respectively. It has also been observed that vitamin E tends to partition preferentially into the olein fraction during fractionation of palm oil. For example, the concentration of vitamin E in RBD palm olein and RBD palm stearin is 104-135% and 57-75%, respectively of the original level of vitamin E in RBD palm oil. See, Sambanthamurthi et al. (2000), "Chemistry and Biochemistry of Palm Oil," *Progress in Lipid Research* 39:507-558, 524 and 547.

In addition to carotenoids, tocotrienols, and tocopherols, crude palm oil also contains 10-80 ppm of the strong antioxidant ubiquinone 10, also known as coenzyme Q10 (CoQ10). Crude palm oil also contains approximately 5 ppm of ubiquinone 9, also known as coenzyme Q9 (CoQ9); however, CoQ9 is not known to have the strong antioxidant effect of CoQ10. Upon fractionation, more CoQ10 is found in the liquid (olein) than in the solid (stearin) fraction. CoQ10 has the following molecular structure:

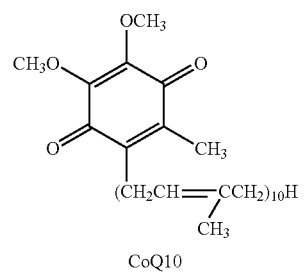

CoQ10

Table 7 shows the content of CoQ10 in crude palm oil and various palm oil products.

TABLE 7

CoQ10 IN PALM OIL PRODUCTS

| SAMPLE | CoQ10 (PPM) |
|---|---|
| Crude palm oil | 10-80 |
| Bleached palm oil | 10-70 |
| RBD palm oil | 10-30 |
| RBD pal olein | 10-20 |
| Palm fatty acid distillate | 0 |
| Residual fiber oil | 5-10 |
| Crude palm kernel oil | 0 |
| Commercial red palm olein | 18-25 |

The foregoing data shows that the levels of CoQ10 decrease with processing. The loss of CoQ10 during processing may be attributable to phosphoric acid and bleaching earth treatment during degumming and high temperature deodorization. Because CoQ10 is not volatile, no CoQ10 is found in the palm fatty acid distillate, which is a by-product of physical refining or in crude palm kernel oil. CoQ10 was found in palm fiber oil and red palm oil and less than 5 ppm of the lower homologue CoQ9 was found in various palm oil fractions, i.e., crude palm oil, bleached palm oil, RBD palm olein, and residual fiber oil.

Squalene ($C_{30}H_{50}$) is a triterpenoid aliphatic hydrocarbon with six unconjugated double bonds. Squalene has been reported to have antioxidant activity and to retard the degradation of unsaturated fatty acids at high temperatures. Squalene is found in high quantities in olive oil (2,400 ppm) and in palm oil products (Table 6). Within the cosmetic industry, squalene is used as a skin lubricant and emollient in creams and lotions. In addition to the foregoing, squalene is also used as an intermediate product for the production of pharmaceuticals. Squalane ($C_{30}H_{62}$), an oily fully saturated material obtained by the catalytic hydrogenation of squalene is used as an ingredient of the oil phase in pharmaceutical creams and lotions both as a skin lubricant and as a carrier of lipid soluble drugs. Squalene and squalane have the following molecular structures:

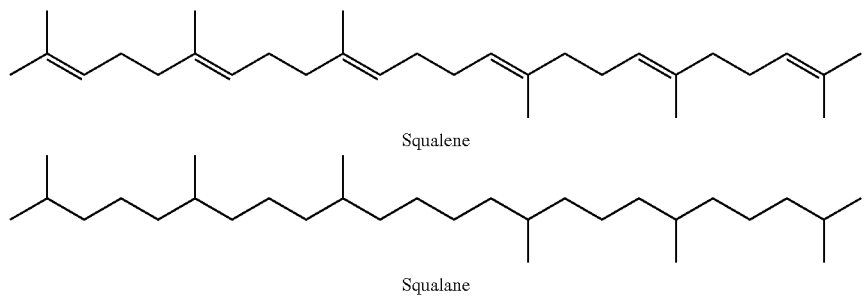

Squalene

Squalane

Table 8 shows the squalene content in palm oil products:

TABLE 8

SQUALENE CONTENT IN PALM OIL PRODUCTS

| OILS AND FATS | SQUALENE (PPM |
|---|---|
| Crude palm oil | 537-659 |
| Bleached palm oil | 530-645 |
| RBD palm oil | 478-791 |
| Palm fatty acid distillate | 2,128-8,191 |

In addition to the foregoing, given the high concentration of squalene in palm fatty acid distillate, it may be possible to recover the hydrocarbon from this refining by-product and introduce the squalene as an additional ingredient in the claimed cosmeceutical formulation.

Sterols are tetracyclic compounds with, typically, 27-29 carbon atoms; sterols make up a sizable portion of the unsaponifiable matter in oil. The sterols in crude palm oil are sitosterol (218-370 ppm), campesterol (90-151 ppm), stigmasterol (44-66 ppm), cholesterol (7-13 ppm), and others (2-18 ppm). Upon refining, their levels are reduced to 68-114 ppm, 26-30 ppm, 12-23 ppm, and 2 ppm, respectively. The total content of sterols in palm oil is about 0.03%. Most of the sterols in palm oil are inert and do not appear to contribute to any important property or behavior of palm oil, although Δ5-avenasterol has been reported to show antioxidant activity in edible oils. See, Sambanthamurthi et al., supra, at 524.

Phospholipids and triterpene alcohols are present in very small amounts in crude palm oil. Phospholipids are present in small quantities (15-130 ppm) in palm oil; however, the phosphorus from phospholipids has been reported as having antioxidant effects. See, Sambanthamurthi et al. at 528. The antioxidant effect of the phospholipids is believed to be the result of the phosphorous chelating pro-oxidant metals. The main phospholipids are phosphatidylcholine, phosphatidylethanolamine, phosphatidylinositol, and phosphatidylglycerol. The unsaponifiable matter in palm oil contains about 0.02% triterpene alcohols. These are a complex group of plant constituents, which consists mainly of five condensed cyclohexane rings with 30 carbon atoms. The triterpene alcohols identified in palm oil are cycloartanol, β-amyrin, cycloartenol, and 2,4-methylene cycloartanol. Although the phospholipids and triterpene alcohols are present in small amounts in crude palm oil, these compounds may play a role in the stability and refinability of palm oil products.

The pronounced antioxidant effect of palm oil is the result the high concentration of unsaturated fats in the oil as well as the high concentration of anti-oxidating agents present in the oil. Unlike polyunsaturated oils, palm oil is more resistant to oxidation because of its higher level of saturated fatty acids (palm oil has a 1:1 ratio of saturated to unsaturated fatty acids). It is the unsaturated fatty acids in the oil that are susceptible to oxidation. The carotenoids, tocopherols, tocotrienols, CoQ10, squalene, squalane, and the antioxidant sterols, phospholipids, and triterpene alcohols present in palm oil act as free radical scavengers and singlet oxygen quenchers. For example, carotenoids quench singlet oxygen through energy transfer from the oxygen to the carotenoid while the quenching mechanism of tocopherols is by charge transfer. The combined effects of the properties of the aforementioned antioxidants confer on palm oil a higher oxidative stability in comparison to many other vegetable oils. In addition to its antioxidant properties, palm oil has also been shown to have antibacterial properties.

II. Optional Components

Additional optional components that may be added to the formulation of the present invention include the following oils: aloe vera oil, apricot oil, apricot kernel oil, avocado oil, black currant oil, borage oil, camellia oil, coconut oil, corn oil, evening primrose oil, flaxseed oil, jojoba oil, meadow foam oil, mineral oil, palm kernel oil, passion fruit oil, passion fruit seed oil, rice bran oil, rose hips oil, safflower oil, soya oil, sunflower oil, tea tree oil, vitamin E oil, and wheat germ oil. Other optional components that may be added to the claimed formulations include the following additives: glycerin, glycerin stearate, lecithin, PEG 100 stearate, lanolin alcohol, petrolatum, vitamin C, and vitamin C ester.

Within the context of the present invention, the preferred oils to be added to the claimed formulations are: evening primrose oil, borage oil, black currant oil, flaxseed oil, safflower oil, and wheat germ oil. The benefits derived from the addition of these oils to the claimed formulations are the presence of high amounts of EFAs that are found in the oils. For example, evening primrose oil is rich in γ-linolenic acid (an omega-6 fatty acid) (9%) and has high concentrations of vitamin E; borage oil and black currant oil are both high in γ-linolenic acid (24% and 15%, respectively); flaxseed oil is rich in α-linolenic acid (an omega-3 fatty acid) (approximately 57%) and α-linoleic acid (an omega-6 fatty acid) (approximately 17%); safflower oil is high in α-linoleic acid (approximately 84%); and wheat germ oil has high concentrations of vitamin E. Any of the oils and additives mentioned herein may be added to the claimed formulations alone or in combination depending on which combinations of EFAs, vitamins, and other properties are desired for the resulting formulation. In addition to the oils listed herein, it is understood that any additional oils high in EFAs may also added to the claimed formulations.

In addition to EFA and vitamin-containing oils, any EFAs may be added directly to the formulation in order to enhance the benefits this important EFA in the formulation. The preferred EFAs to be added directly to the claimed formulation are α- and/or γ-linolenic acid.

Esterification of fatty acids and alcohols allows the manufacture of straight and branched chain, mono-, di-, tri-, and tetraesters, which are used to modify the look and feel of formulations. Depending on the chain length and structural arrangement of the fatty acids and alcohols, esters can be tailored to provide different physical properties and types of emollience. For example, the straight chain esters cetyl palmitate and cetostearyl stearate, which are solid at room temperature, may be used to increase the viscosity of emulsions and impart a dry emollience to skin. Liquid branched chained esters, such as isopropyl myristate and cetostearyl ethylhexanoate, provide non-occlusive emollience with good spreading properties. Pentaerythrityl tetraisostearate, a high molecular weight tetraester, confers a long-lasting emollience to skin creams and lotions.

For suncare formulations, the choice of emollient influences both the solubility and spreadability of the sunscreen agent and its ability to penetrate the skin. Due to polarity, certain fatty acid esters are excellent solvents for organic sunscreens. Preferred esters for sunscreen formulations are caprylic/capric triglyceride, octyl methoxycinnamate benzophenone-3, ethylhexyl hydroxystearate, and esters of C12-C15 alkyl benzoate. Complete solubilization of the sunscreen in the formulation helps promote even application on the skin and enhance SPF performance.

Natural plant and animal waxes may be added to the claimed formulations as an additional hardening agent. Waxes are harder, more brittle, and have higher melting points than fats. Common waxes added to cosmetics include carnuba wax and beeswax. As an alternative, synthetic waxes such as ethylene glycol diesters or triesters of long-chain (C18-C36) fatty acids offer functional alternatives. With melting points ranging between 60-75° C., they can be used to confer a high degree of rigidity to stick systems and to modify the product's crystallinity.

An common wax used in cosmetics is lanolin, a woolfat. Lanolin bear chemical and physical similarities to the stratum corneum lipids of the skin, which as mentioned above, prevent transepidermal water loss. As such, lanolin is frequently used as a skin emollient and moisturizing agent in cosmetics. Ethyoxylated lanolins have been found to be effective in reducing the irritating effects of surfactants in detergent systems and thus are frequently added to soaps.

Citric acid may be added to the claimed formulations to improve oxidative properties. Because citric acid is an effective chelating agent, it serves to deactivate the catalytic activities of pro-oxidant metals such as copper and iron that may be present in the formulation.

It is best to add anti-oxidants to the palm oil products of the present invention at the cooling stage after deodorization when the temperature of the palm oil product is 120° C. or cooler. To avoid any caustic effects that may result from the acidic properties of citric acid, the anti-oxidant should be thoroughly dispersed within the palm oil product.

III. Amounts and Properties

The topical formulation of the claimed invention will be a cosmeceutically acceptable topical formulation comprising a semi-solid admixture of palm oil, palm olein, and palm stearin, wherein the formulation is substantially homogeneous and begins to liquefy at a temperature above 80° F., preferably 85° F., more preferably above 90° F., and most preferably above 95° F. The palm oil for use in the formulation may be selected from crude palm oil, RBD palm oil, NBD palm oil, chemically modified versions thereof, and mixtures of any of the foregoing. The preferred palm oil for use in the claimed formulations is RBD palm oil and chemically modified versions thereof. The chemically modified versions of RBD palm oil may be selected from RBD palm oil, interesterified RBD palm oil, transesterified RBD palm oil, partially hydrogenated RBD palm oil, partially alkoxylated RBD palm oil, and mixtures thereof, with RBD palm oil and interesterified RBD palm oil preferred. The palm olein is selected from red palm olein, red palm super olein, red palm top olein, and mixtures thereof, with red palm super olein preferred. For the preparation of the cream formulation of the present invention, it is preferred to use palm stearin as the main ingredient to ensure that the formulation retains a semi-solid consistency at room temperature.

To avoid hydrolysis, the preferred formulation will be substantially water-free. Further, as the preferred formulation is an all-natural product, it will necessarily be free of synthetic additives. As mentioned above, the formulation may contain additional oils, EFAs, natural waxes, and citric acid to enhance the antioxidant effects of the formulation or to improve the texture and consistency of the formulation. As previously mentioned, the preferred additional oils to be added to the claimed formulations are evening primrose oil, borage oil, black currant oil, flaxseed oil, safflower oil, and wheat germ oil and the preferred EFAs to be added to the claimed formulations are α- and γ-linolenic acid with γ-linolenic acid being most preferred.

IV. Manufacturing Processes

The present inventors have found, surprisingly, that by votating RBD or NBD palm oil or RBD or NBD palm stearin, alone or in combination, together with a red palm olein, a homogeneous formulation results, which has all the benefits of the anti-oxidants found in crude palm oil without the formation of the crystallized materials or the deep red pigments that are inherent in the crude palm oil products. Votating is the term used to describe the process for continuous chilling and crystallizing of fats and oils using scraped-surface heat exchangers. Under the votating procedure, oils or fats are passed through a heat exchanger and rapidly chilled to the point of being supercooled. The resulting crystallized product is extruded to form a creamy and homogeneous blend. Commercial examples of votated fats include margarine and shortenings.

In a first embodiment of the present invention, there is provided a biocompatible, cosmeceutically acceptable topical formulation comprising a votated blend of a palm oil and a red palm olein, wherein the formulation is substantially homogeneous. In this embodiment, the formulation may be in the form of a cream, lotion, sunscreen, soap, or any other form acceptable for use in a cosmeceutical context. While it is preferred that the product is an all natural product, the addition of synthetic additives may be added to the formulation if necessary. Also, if desired or necessary, the palm oil may be interesterified to tailor the melting point of the formulation or to adjust the consistency so that the formulation will dissolve readily into the skin; within the context of the present invention, interesterification does not alter the natural state of the formulation. As mentioned above, the interesterification process has the advantage of improving the epidermal EFA concentration of the resulting formulation. Although a less preferred fat-tailoring procedure to interesterification, the formulation may also be partially hydrogenated to increase the fraction of the solid phase, and/or partially alkoxylated to adjust the fluidity of the formulation. Hydrogenation, alone or together with alkoxylation has the added advantage of increasing the oxidative and shelf-life of the resulting formulation.

In a second embodiment of the present invention, there is provided a biocompatible, cosmeceutically acceptable topical formulation comprising a votated blend of: (a) approximately 85 wt. % to 99 wt. % of an RBD palm stearin; (b) approximately 0.5 wt. % to 10 wt. % of a red palm olein; (c) approximately 0.5 wt. % to 5.0 wt. % of an additional oil; and optionally (d) approximately 0.5 wt. % to 5.0 wt. % of an individual fatty acid, wherein the formulation is substantially homogeneous, substantially free of crystallized components, and begins to liquefy at a temperature no lower than 80° F. In this embodiment, the resulting formulation is preferably a cream with a smooth homogeneous texture that has a melting point at or above body temperature. As palm stearin has a melting point of 50-54° C. (122-129.2° F.), under this embodiment, interesterification of the RBD palm oil prior to fractionation should generally not be required to raise the melting point temperature of the formulation but may be used to tailor the consistency of the formulation if desired. As an alternative to interesterification to alter the consistency of the formulation, different combinations of RBD palm hard, super, and soft stearin may be used.

In a third embodiment of the present invention, there is provided a biocompatible, cosmeceutically acceptable topical formulation comprising a votated blend of: (a) approximately 85 wt. % to 99 wt. % of an RBD palm oil; (b) approximately 0.5 wt. % to 10 wt. % of a red palm olein; (c) approximately 0.5 wt. % to 5.0 wt. % of additional oil; and optionally (d) approximately 0.5 wt. % to 5.0 wt. % of an individual fatty acid, wherein the formulation is substantially homogeneous, substantially free of crystallized components, and begins to liquefy at a temperature no lower than 80° F. In this embodiment, the resulting formulation is preferably a lotion with a smooth homogeneous texture that has a melting point at or above body temperature. Because palm oil has a melting point of 33-39° C. (91.4-102.2° F.), to ensure that the lotion does not liquefy in a warm room but rather maintains a uniform consistency throughout the formulation's shelf-life, interesterification alone or in combination with partial hydrogenation and/or partial alkoxylation may be necessary.

In a fourth embodiment, there is provided a biocompatible, cosmeceutically acceptable topical formulation comprising a votated blend of: (a) approximately 50 wt. % to 75 wt. % of an RBD palm oil; (b) approximately 24 wt. % to 35 wt. % of RBD palm stearin; (c) approximately 0.5 wt. % to 10 wt. % of a red palm olein; (d) approximately 0.5 wt. % to 5.0 wt. % of additional oil; and optionally (e) approximately 0.5 wt. % to 5.0 wt. % of an individual fatty acid, wherein the formulation is substantially homogeneous, substantially free of crystallized components, and begins to liquefy at a temperature no lower than 80° F. In this embodiment, the resulting formulation is preferably lotion with a smooth homogeneous texture that has a melting point at or about body temperature. The melting point temperature of this formulation as well as the consistency and texture, are preferably adjusted by altering the amount of RBD palm stearin in the formulation; however, as mentioned above, the structured lipid approaches of interesterification alone or in combination with partial hydrogenation and/or alkoxylation may also be used if desired.

Within the context of the claimed invention, it is understood that the claimed palm oil may be crude palm oil, RBD palm oil, NBD palm oil or chemically modified forms thereof; the RBD palm oil may be replaced with NBD palm oil or chemically modified forms thereof; the red palm olein may be substituted with red palm super olein, or red palm top olein; and the RBD palm stearin may be either RBD palm hard stearin, RBD palm super stearin, RBD palm soft stearin, or combinations thereof.

Each of the creams or lotions described above may be made into a sunscreen through the addition of an appropriate compound having an SPF. As mentioned above, the addition of esterified fatty acids may assist in the solubility of the sun protection compound into the cosmeceutical formulation.

The formulation of the present invention may also be made into a soap by way of an alcoholysis reaction between palm oil and methanol (methanolysis) to produce palm oil fatty acid methyl esters. The methyl esters may then by saponified to produce a soap containing all of the antioxidant benefits of the claimed cosmeceutical formulations.

V. Utility

The claimed formulations may be topically applied to the skin of an individual in need of treatment for local skin conditions such as dryness, flakiness, hyperpigmentation, photodamaged skin, sunburn, windburn, irritation, itchiness (e.g., from a rash, an insect bite, etc.), roughness, and hardened skin (e.g., calluses). The claimed formulations may also be topically applied to the skin of an individual in need of treatment for inflammatory diseases such as sebaceous gland disorders, e.g., acneiform disorders such as acne vulgaris, acne rosacea, and seborrhea; papulosquamous dermatoses such as psoriasis; autoimmune dermatoses such as discoid lupus erythematosus or systemic lupus erythematosus; and other inflammatory disorders, including dermatoses manifested by eczema, e.g., eczematoid dermatitis. In addition to the foregoing, the claimed formulations are also effective for everyday uses such as for the care and treatment of diaper rash and chapped lips and for general moisturizing, softening, and improving appearance of the skin. The claimed formulations are also used to improve aging-related skin conditions, such as wrinkles, lines, loss of skin elasticity, age spots, etc.

In practical terms, thus, the claimed invention may be used to increase the recovery time associated with bruising, burns, and cuts; to the trauma to skin associated with scab formation; to alleviate the discomforts of scar tissue (such as the tightness associated with scarring); to reduce the discoloration of scar tissue; to alleviate the parched skin associated with chemotherapy and radiation treatment; to alleviate the redness and scaling associated with psoriasis and extremely dry skin (such as on elbows and the soles of the feet); and to alleviate the spreading and itching associated with eczema.

Because the claimed formulations contain a high percentage of carotenoid and vitamin E antioxidants, it is an effective vehicle for the delivery of carotenoids and vitamin E tocotrienols and tocopherols to the skin of an individual.

VI. Regimen

The claimed formulations may be applied to an individual's skin within a region in which skin moisturization, softening, or soothing is desired. Such a region may be applied to the skin on the face, including the lips, or to a region that has been subjected to an insect bite. The formulation may be applied on an as-needed basis or periodically over an extended period of time, such as at least once a day or once a week. It is preferred to apply the cosmeceutical formulation of the present invention as frequently as possible.

For application of the formulation of the present invention to facial skin, the following regimen is preferred: cleanse face thoroughly with a mild cleanser, apply a moderate layer of the cream formulation of the present invention, rinse face with hot water, rinse face with approximately twelve splashes of ice water or very cold water, pat face dry, apply a thin layer of the cream formulation. For women, make-up may be applied on top of the cream.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein, both supra and infra, are hereby incorporated by reference in their entireties.

VII. Experimental

Example 1

The following ingredients are combined and votated to form a cream for topical application to the skin:

| INGREDIENT | AMOUNT |
| --- | --- |
| RBD Palm Stearin | 95 wt. % |
| Red Palm Super Olein | 3 wt. % |
| Evening Primrose Oil | 0.5 wt. % |
| Safflower Oil | 0.5 wt. % |
| Wheat Germ Oil | 0.5 wt. % |
| γ-Linolenic Acid | 0.5 wt. % |

Example 2

The following ingredients are combined and votated to form a cream for topical application to the skin:

| INGREDIENT | AMOUNT |
| --- | --- |
| RBD Palm Stearin | 95 wt. % |
| Red Palm Super Olein | 1 wt. % |
| Evening Primrose Oil | 1 wt. % |
| Safflower Oil | 1 wt. % |
| Wheat Germ Oil | 1 wt. % |
| γ-Linolenic Acid | 1 wt. % |

Example 3

The following ingredients are combined and votated to form a cream for topical application to the skin:

| INGREDIENT | AMOUNT |
| --- | --- |
| RBD Palm Stearin | 94 wt. % |
| Red Palm Super Olein | 5 wt. % |
| Evening Primrose Oil | 0.25 wt. % |
| Safflower Oil | 0.25 wt. % |
| Wheat Germ Oil | 0.25 wt. % |
| γ-Linolenic Acid | 0.25 wt. % |

Example 4

The following ingredients are combined and votated to form a lotion for topical application to the skin:

| INGREDIENT | AMOUNT |
| --- | --- |
| RBD Palm Oil | 72 wt. % |
| RBD Palm Stearin | 23 wt. % |
| Red Palm Super Olein | 3 wt. % |
| Evening Primrose Oil | 0.5 wt. % |
| Safflower Oil | 0.5 wt. % |
| Wheat Germ Oil | 0.5 wt. % |
| γ-Linolenic Acid | 0.5 wt. % |

Example 5

The following ingredients are combined and votated to form a lotion for topical application to the skin:

| INGREDIENT | AMOUNT |
| --- | --- |
| RBD Palm Oil | 75 wt. % |
| RBD Palm Stearin | 20 wt. % |
| Red Palm Super Olein | 1 wt. % |
| Evening Primrose Oil | 1 wt. % |
| Safflower Oil | 1 wt. % |
| Wheat Germ Oil | 1 wt. % |
| γ-Linolenic Acid | 1 wt. % |

Example 6

The following ingredients are combined and votated to form a lotion for topical application to the skin:

| INGREDIENT | AMOUNT |
| --- | --- |
| RBD Palm Oil | 91 wt. % |
| Red Palm Super Olein | 5 wt. % |
| Evening Primrose Oil | 1 wt. % |
| Safflower Oil | 1 wt. % |
| Wheat Germ Oil | 1 wt. % |
| γ-Linolenic Acid | 1 wt. % |

Prior to votating, the RBD palm oil is interesterified to raise the melting point temperature of the RBD palm oil and if desired or necessary, partially hydrogenated-alkoxylated to adjust the consistency of the RBD palm oil and increase the oxidative stability and shelf-life of the resulting formulation.

Example 7

The following ingredients are combined and votated to form a sunscreen lotion with an SPF 15 for topical application to the skin:

| INGREDIENT | AMOUNT |
| --- | --- |
| RBD Palm Oil | 88 wt. % |
| Red Palm Super Olein | 2 wt. % |
| Octyl Methoxycinnamate | 2.5 wt. % |
| Benzophenone 3 | 2.5 wt. % |
| Ethylhexyl Hydroxystearate | 1 wt. % |
| Evening Primrose Oil | 1 wt. % |
| Safflower Oil | 1 wt. % |
| Wheat Germ Oil | 1 wt. % |
| γ-Linolenic Acid | 1 wt. % |

Prior to votating, the RBD palm oil is interesterified to raise the melting point temperature of the RBD palm oil and if desired or necessary, partially hydrogenated-alkoxylated to adjust the consistency of the RBD palm oil and to increase the oxidative stability and shelf-life of the resulting formulation.

Example 8

The following ingredients are combined to form a soap:

| INGREDIENT | AMOUNT |
| --- | --- |
| RBD Palm Oil | 90 wt. % |
| Red Palm Super Olein | 5 wt. % |
| Evening Primrose Oil | 2 wt % |
| Safflower Oil | 1 wt. % |
| Wheat Germ Oil | 1 wt. % |
| γ-Linolenic Acid | 1 wt. % |

The mixture is votated then subjected to methanolysis followed by saponification.

We claim:

1. A biocompatible topical formulation comprising a votated blend of a fractionated or unfractionated palm oil, or both, and a red palm olein,
wherein the formulation is at least 90% homogeneous;
wherein the palm oil represents approximately 90 wt. % to 99.5 wt. % of the formulation and the red palm olein represents approximately 0.5 wt. % to 10 wt. % of the formulation;
wherein the unfractionated palm oil is selected from the group consisting of crude palm oil, RBD palm oil, NBD palm oil, and the fractionated palm oil is selected from the group consisting of RBD palm olein, RBD palm stearin, NBD palm olein, NBD palm stearin, chemically modified versions of any of the foregoing thereof, and mixtures of any of the foregoing; and wherein the formulation is for applying to skin of a human.

2. The formulation of claim 1, wherein the formulation is at least 90% water-free.

3. The formulation of claim 1, wherein the formulation is at least 90% free of crystallized components.

4. The formulation of claim 1, wherein the formulation is free of synthetic additives.

5. The formulation of claim 1, wherein formulation begins to liquefy at a temperature no lower than 80° F.

6. The formulation of claim 1, wherein the palm oil is RBD palm stearin.

7. The formulation of claim 1, wherein the palm oil is RBD palm oil and chemically modified versions thereof.

8. The formulation of claim 7, wherein the palm oil is selected from RBD palm oil, interesterified RBD palm oil, partially hydrogenated RBD palm oil, partially alkoxylated RBD palm oil, and mixtures thereof.

9. The formulation of claim 8, wherein the palm oil is selected from RBD palm oil, interesterified RBD palm oil, and mixtures thereof.

10. The formulation of claim 1, wherein the red palm olein is red palm super olein or red palm top olein.

11. The formulation of claim 10, wherein the red palm olein is red palm super olein.

12. The formulation of claim 1, wherein the palm oil is RBD palm stearin and the red palm olein is red palm super olein.

13. The formulation of claim 1, further comprising an additional component selected from additional oils, individual fatty acids, and combinations thereof.

14. The formulation of claim 13, wherein the additional component is an additional oil.

15. The formulation of claim 14, wherein the additional oil is selected from evening primrose oil, borage oil, black currant oil, flaxseed oil, safflower oil, wheat germ oil, and mixtures thereof.

16. The formulation of claim 13, wherein the additional component is an individual fatty acid.

17. The formulation of claim 16, wherein the fatty acid is γ-linoleic acid.

18. A method of delivering a carotenoid to the skin of a mammalian individual, comprising topically applying the formulation of claim 1 to the individual's skin.

19. A method for treating a skin condition comprising topically applying the formulation of claim 1 to the skin of an individual in need of such treatment.

20. The method of claim 18, wherein the skin condition is selected from dryness, flakiness, wrinkles, hyperpigmentation, photodamaged skin, sunburn, windburn, irritation, itchiness, roughness, and hardened skin.

21. The method of claim 20, wherein the skin condition is an inflammatory dermatosis.

22. The method of claim 21, wherein the inflammatory dermatosis is acne vulgaris.

23. The method of claim 21, wherein the inflammatory dermatosis is acne rosacea.

24. The method of claim 21, wherein the inflammatory dermatosis is psoriasis.

25. The method of claim 21, wherein the inflammatory dermatosis is eczematoid dermatitis.

26. The method of claim 18, wherein the skin condition is diaper rash.

27. A method for moisturizing the skin, comprising topically applying the formulation of claim 1 to an individual's skin within a region in which skin moisturization is desired.

28. A method for softening the skin, comprising topically applying the formulation of claim 1 to an individual's skin within a region in which skin softening is desired.

29. A method for treating chapped lips, comprising applying the formulation of claim 1 to the lips of an individual in need of such treatment.

30. A method for soothing the skin, comprising topically applying the formulation of claim 1 to an individual's skin within a region in which soothing is desired.

31. The method of claim 30, wherein the region to which the formulation is applied contains an insect bite.

32. A method for improving the appearance of facial skin, comprising topically applying the formulation of claim 1 to the facial skin of an individual desirous of such improvement.

33. A method for treating an aging-related skin condition, comprising topically applying the formulation of claim 1 to the skin of an individual in need of such treatment.

34. The method of any one of claims 18, 19, 27, 28, 29, 30, 32, and 33, wherein the formulation is applied on an as-needed basis.

35. The method of any one of claims 18, 19, 27, 28, 29, 30, 32, and 33, wherein the formulation is applied at least once a day over an extended time period.

* * * * *

UNITED STATES PATENT AND TRADEMARK OFFICE
CERTIFICATE OF CORRECTION

PATENT NO.        : 8,524,292 B2                                                      Page 1 of 1
APPLICATION NO.   : 12/402330
DATED             : September 3, 2013
INVENTOR(S)       : Kopas et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 687 days.

Signed and Sealed this
Twenty-fourth Day of February, 2015

Michelle K. Lee
*Deputy Director of the United States Patent and Trademark Office*